(12) United States Patent
Blumberg et al.

(10) Patent No.: US 11,739,084 B2
(45) Date of Patent: Aug. 29, 2023

(54) SYNTHETIC ROUTE TO SCOPOLAMINE AND/OR ATROPINE

(71) Applicant: Southwest Research Institute, San Antonio, TX (US)

(72) Inventors: Shawn T. Blumberg, San Antonio, TX (US); Paul W. Miguel, San Antonio, TX (US); Daniel A. Hinojosa, Zapata, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 17/450,254

(22) Filed: Oct. 7, 2021

(65) Prior Publication Data

US 2023/0121306 A1    Apr. 20, 2023

(51) Int. Cl.
*C07D 451/10*    (2006.01)

(52) U.S. Cl.
CPC .................................. *C07D 451/10* (2013.01)

(58) Field of Classification Search
CPC .................................................. C07D 451/10
See application file for complete search history.

(56) References Cited

U.S. PATENT DOCUMENTS 4,001,249 A    1/1977 Noyori et al.

OTHER PUBLICATIONS

Dobo, et al., "The Stereochemistry of the Tropane Alkaloids. Part XII. The Total Synthesis of Scopolamine", 1959, pp. 3461-3465.
Hayakawa, et al., "General Synthesis of Tropane Alkaloids via the Polybromo Ketone-Iron Carbonyl Reaction", Journal of the American Chemical Society, 100:6, 1978, pp. 1786-1791.
Nocquet, et al., "Total Synthesis of (±)-Scopolamine: Challenges of the Tropane Ring", European Journal of Organic Chemistry, 2016, pp. 1156-1164.
Schink, et al., "Stereocontrolled Epoxidations of Cycloheptene Derivatives in the Palladium-Catalyzed Route to Tropane Alkaloids. Total Syntheses of Scopine and Pseudoscopine", Journal of Organic Chemistry, vol. 56, No. 8, 1991, pp. 2769-2774.
Ulrich, et al., "Scopolamine: A Journey from the Field to Cinics", Phytochem Rev, 16, Springer Publishing Co., 2017, pp. 333-353.

*Primary Examiner* — Paul V Ward
(74) *Attorney, Agent, or Firm* — Grossman, Tucker, Perreault & Pfleger, PLLC

(57) ABSTRACT

A synthetic route to scopolamine and/or atropine. In such context, the present invention identifies a method for preparing 6,7-dehydro atropine, which can be converted into either scopolamine and/or atropine, along with a method for converting a protected pyrrole into a tetrachlorobicylic compound, such as benzyl 3-oxo-8-azabicyclo[3.2.1]oct-6-ene-8-carboxylate.

12 Claims, 1 Drawing Sheet

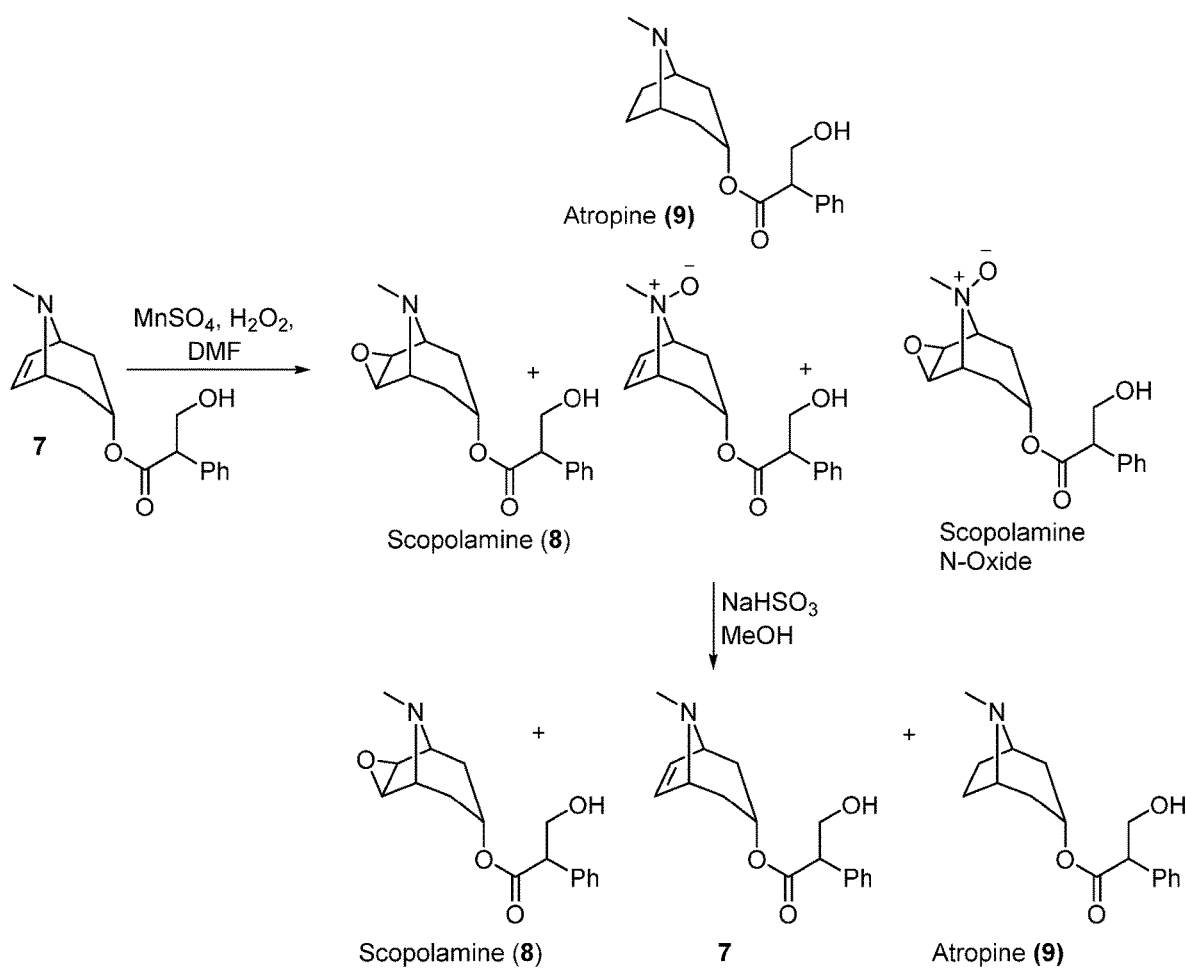

SYNTHETIC ROUTE TO SCOPOLAMINE AND/OR ATROPINE

FIELD

The present invention is directed to a synthetic route to scopolamine and/or atropine. In such context, the present invention identifies a method for preparing 6,7-dehydro atropine, which can be converted to either scopolamine and/or atropine. Also disclosed is a method for converting a protected pyrrole into a tetrachlorobicylic compound, such as benzyl 3-oxo-8-azabicyclo[3.2.1]oct-6-ene-8-carboxylate.

BACKGROUND

In the 1970's, the department of defense (DOD) developed the Mark 1 nerve agent antidote kit which contained atropine and 2-PAM 2:

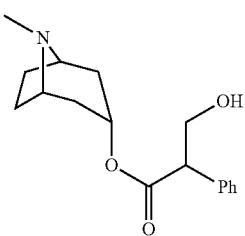

Atropine

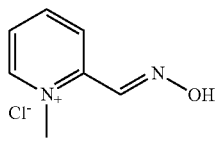

2-PAM

Atropine protects against the surge of acetylcholine by blocking the acetylcholine receptor sites in the synapse (called antagonism) while 2-PAM 2 reactivates the inhibited AChE. Atropine primarily interacts with the muscarinic receptors (a receptor sub-type), which protects the heart and the lungs from the effects of organophosphorous nerve agents (OPNAs). Unfortunately, it does not interact with the nicotinic receptors (another receptor sub-type) which are located primarily in the brain and central nervous system (CNS), leaving the brain critically unprotected during OPNA exposure. Recent studies on (−)-scopolamine, however, have shown that it interacts with the nicotinic receptors, making it an attractive candidate for protection against OPNA CNS symptoms.

Currently scopolamine is isolated from plants in the Solanaceae family, such as belladonna (*Atropa belladonna*) and the corkwood tree (*Duboisia leichhardtii*). See, S. F. Hagels, H. Hagels and O. Kayser, Phytochem Rev 2017, 16, 333-353.

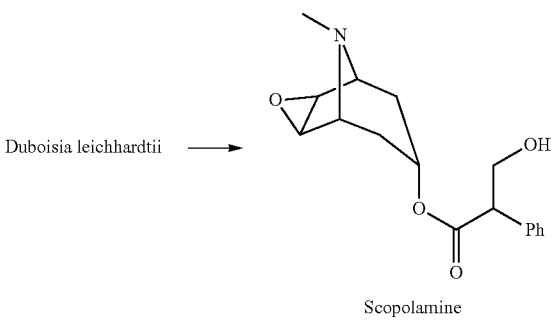 [SMILES: CN1C2CC(OC(=O)C(CO)c3ccccc3)CC1C1OC12]

Scopolamine

These plants must be farmed, dried, pulverized and the compounds extracted and purified by chromatography to yield only 2-4% (w/w) scopolamine which generates significant waste. Two corporations, Boehringer Ingelheim and Alkaloids corporation have reported on processes that accomplish this approach, but the high demand coupled with the relatively slow growth rates of the plant have made it relatively difficult to procure the quantities needed to evaluate this compound as an OPNA antidote. Additional problems in the supply have been encountered due to yearly crop yield fluctuations as a result of adverse weather events, pests, or disease. Moreover, the global demand for scopolamine (3) is estimated to be about 2450 kg, which is anticipated to grow. Isolation for natural sources, however, will likely become more relatively expensive on larger scales There are other relevant prior art reaction sequences that have been reported in the literature. See, Hayakawa, Y.; Baba, Y.; Makino, S.; and Noyori, R., *J Am Chem Soc.* 1978, 100 1786-1791. Here, Noyori utilized a reductive dipolar cycloaddition between a carbomethoxypyrrole and tetrabromoacetone to form, after dehalogenation, the tropenone. Reduction of the tropenone with diisobutyl aluminum hydride (DIBAL-H) then furnished 6-tropen-3α-ol or 8-methyl-8-azabicyclo[3.2.1]oct-6-en-3-ol.

In addition, reference is made to the work of Dobo et al, which reported on a synthesis of scopolamine, starting from tropane-3α,6β-diol, which was converted into 3α-acetoxy-6-ene and then into O-acetylscopine (3α-acetoxy-6β,7β-epoxytropane). Hydrolysis, followed by acylation with O-acetyltropoyl chloride and hydrolysis gave scopolamine. See, Dobo, P.; Fodor, G.; Janzso, G.; Koczor, J.; Toth, J.; and Vincze, I., J. Chem. Soc. 1959, 3461-3465. Some weaknesses of this approach are considered to be the use of acetates to protect parts of the molecules from reaction, and the use of $Fe_2(CO)_9$ and tetrabromoacetone, both of which are relatively expensive and relatively toxic.

Accordingly, it is an objective of the present invention to develop an alternative approach for the synthesis of scopolamine and/or atropine, along with underlying intermediate reactions that facilitate such goal.

SUMMARY

A method for preparing 6,7-dehydro atropine comprising:

(a) providing a protected pyrrole having the following formula:

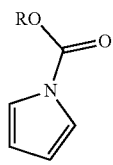

wherein R may be an alkyl group, phenyl group, or benzyl group;

(b) reacting the protected pyrrole with pentachloroacetone and forming a first tetrachloro-bicyclic compound having the following formula:

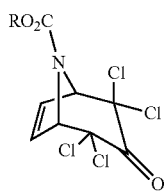

wherein R may be an alkyl group, phenyl group, or benzyl group (c) carrying out a reductive dechlorination of the first tetrachloro-bicyclic compound and forming a second bicyclic compound having the following formula:

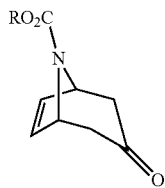

wherein R may be an alkyl group, phenyl group, or benzyl group;

(d) carrying out a reductive methylation of the second bicyclic compound formed in step (c) and forming or 8-methyl-8-azabicyclo[3.2.1]oct-6-en-3-ol having the following formula:

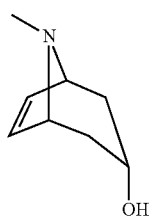

(e) converting 8-methyl-8-azabicyclo[3.2.1]oct-6-en-3-ol into 6,7-dehydro tropene tosylate having the following formula:

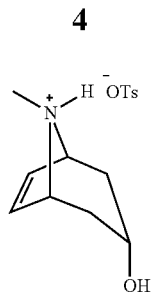

wherein ⁻OTs is reference to $^-OSO_2$—Ar—$CH_3$; and (f) converting 6,7-dehydro tropene tosylate into 6,7-dehydro atropine having the following formula:

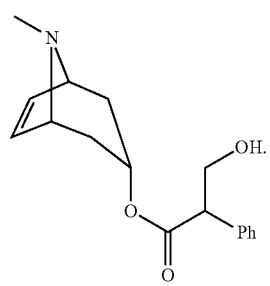 [SMILES: CN1C2C=CC1CC(OC(=O)C(CO)c1ccccc1)C2]

A method of converting a protected pyrrole into a tetrachlorobicylic compound comprising:

a. providing a protected pyrrole having the following formula:

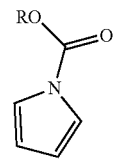

wherein R may be an alkyl group, phenyl group, or benzyl group;

b. reacting the protected pyrrole with pentachloroacetone and forming a tetrachloro-bicyclic compound having the following formula:

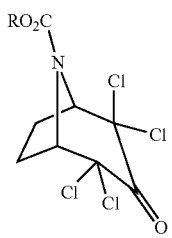

wherein R may be an alkyl group, phenyl group, or benzyl group.

BRIEF DESCRIPTION OF THE DRAWING

FIG. 1. illustrates the oxidation of compound 7, 6,7-dehydro atropine, followed by a reductive work-up.

DETAILED DESCRIPTION

The present invention is directed to a synthetic route to scopolamine and/or atropine. In the initial step, a protected pyrrole is provided. One can therefore utilize an alkyl, phenyl or benzyl carbamate protected pyrrole which can be achieved by treatment of pyrrole with a substituted chloroformate Cl—CO—OR, where R can be an alkyl group (e.g. methyl, ethyl propyl), a phenyl group, a substituted phenyl group, or a benzyl group:

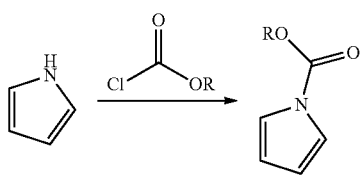

Preferably, the pyrrole herein is protected by treatment with sodium hydride followed by quenching upon addition of benzyl chloroformate (ClCOOBn) at −78° C., in a preferred tertiary butanol (tBuOH) and tetrahydrofuran (THF) solvent media, to yield a benzyl carbamate protected pyrrole at yields of around 95%:

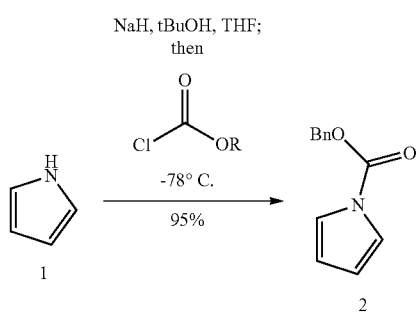

In the next step shown below, the preferred benzyl carbamate protected pyrrole 2 is reacted with pentachloroacetone (PCA or Cl$_3$COC(Cl)$_2$H) in the preferred solvent hexafluoroisopropanol (HFIPA) in the presence of the preferred organic base N-methylmorpholine (NMM), which organic base is preferably at a concentration of 0.5 M, providing the compound 3, benzyl 2,2,4,4-tetrachloro-3-oxo-8-azabicyclo[3.2.1]oct-6-ene-8-carboxylate, in 86% yield:

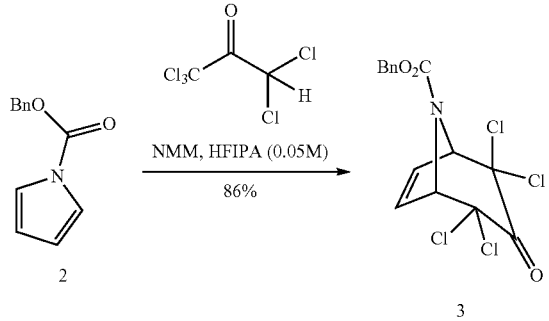

With regards to the use of pentachloroacetone (PCA) for the conversion of compound 2 to compound 3, it was recognized herein that the PCA can be preferably prepared from hexachloroacetone (HCA), in situ, in the presence of a trialkyl- or triaryl-phosphite having the formula POR$_3$ where R can be an alkyl group (e.g., methyl, ethyl, propyl) or a phenyl moiety. A particularly preferred phosphite is triphenylphosphite (P(OPh)$_3$). In addition, one may utilize a trialkyl- or triaryl phosphine having the formula PR$_3$ where R can again be alkyl groups (e.g., methyl, ethyl propyl) or a phenyl moiety.

Reductive dechlorination of benzyl 2,2,4,4-tetrachloro-3-oxo-8-azabicyclo[3.2.1]oct-6-ene-8-carboxylate provides compound 4, benzyl 3-oxo-8-azabicyclo[3.2.1]oct-6-ene-8-carboxylate, in greater than 90% yield. More specifically, compound 3 is exposed to a reducing agent, preferably Zn, a tertiary amine (NR$_3$ wherein R is an alkyl group such as a methyl, ethyl and/or propyl group), more preferably tetramethylene diamine (TMEDA), an organic acid such as acetic acid (AcOH), in an organic alcohol such as methanol (MeOH) according to the following reaction scheme:

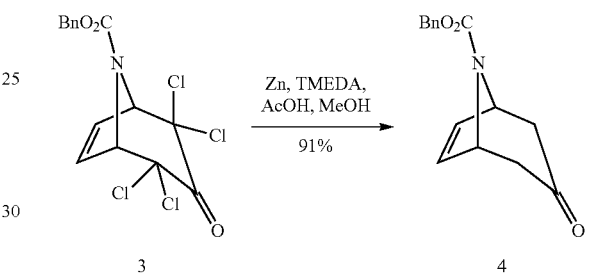

Reductive methylation of compound 4 and formation of a tosylate salt follows. Preferably, compound 4 is reacted in tetrahydrofuran solvent (THF) in the presence of dibutyl aluminum hydroxide (DIBAL-H) to reduce the ketone moiety followed by addition of lithium aluminum hydride (LiALH$_4$) to reduce the carbamate, at preferred reaction temperatures of −78° C. to room temperature (r.t.), resulting in compound 5 (6-tropen-3α-ol or 8-methyl-8-azabicyclo [3.2.1]oct-6-en-3-ol), at yields of at or over 80%:

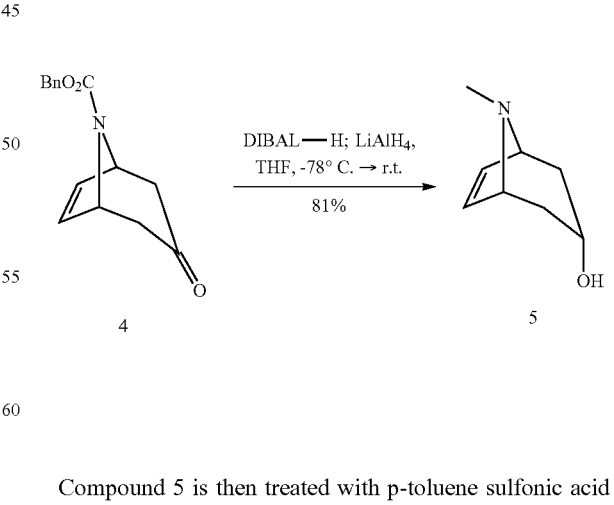

Compound 5 is then treated with p-toluene sulfonic acid (pTSA) in a preferred acetone solvent which provides compound 6, 6,7-dehydro tropene tosylate, at yields of at or over 65%. In the formula below, $^-$OTs is reference to $^-$OSO$_2$—Ar—CH$_3$:

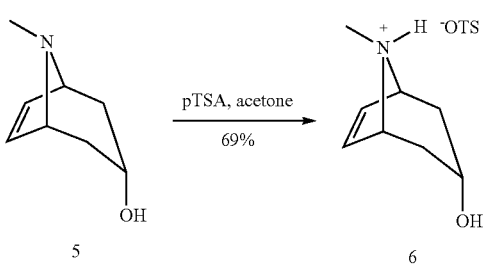

Compound 6 is then converted to compound 7, 6,7-dehydro atropine, at yields of at or above 80.0%. Specifically, coupling of tropic acid to compound 6 was preferably achieved by use of tropic acid having an organo-silicon protective group. One therefore preferably employs a tert-butyldimethylsilyl (TBS) protected tropic acid which then can reduce the risk of side reactions that may occur during its removal. This coupling reaction preferably proceeds in the presence of methylnitrobenzoic acid anhydride (MNBA), triethyl amine (TEA), in an organic solvent, such as methylene chloride. Then, deprotection of the organo-silicon protective group proceeds via the use of methanol (MeOH) buffered with acetic acid (AcOH) in the presence of ammonium fluoride ($NH_4F$).

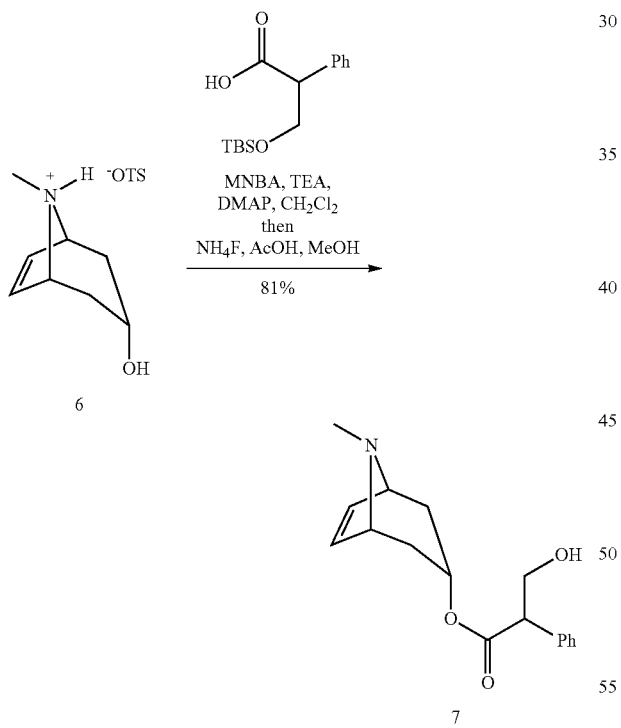

Compound 7, 6,7-dehydro atropine, can then be converted into compound 8, scopolamine and/or compound 9, atropine. The conversion to scopolamine preferably proceeds via oxidation of compound 7 in an organic solvent. Preferably, oxidation in the presence of manganese sulfate ($MnSO_4$) and hydrogen peroxide ($H_2O_2$) in an organic solvent (DMF) in the presence of sodium bicarbonate followed by a reductive work-up with sodium hydrogen sulfite ($NaHSO_3$) in methanol (MeOH), which provides a 25% yield of scopolamine (46% based on recovered starting material). The reductive work-up with $NaHSO_3$ reduced the amine oxides of compound 7, 8, 9 back to the corresponding amines. The general scheme is set out below. The more specific scheme is illustrated in FIG. 1.

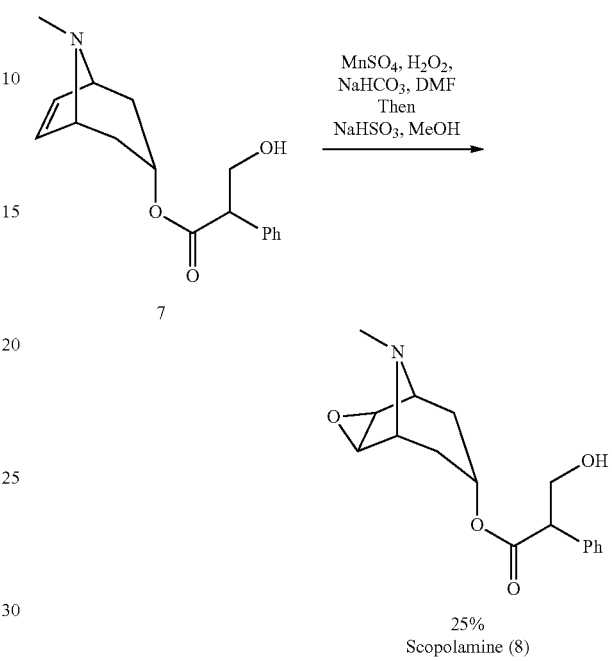

In addition, it is contemplated that the $MnSO_4$ in the above reaction scheme may be utilized, preferably at a 1:1 molar ratio, with a ligand, from the family of porphyrin, diamine and picolinic acid compounds illustrated below, where R may be an alkyl group (e.g., methyl, ethyl, propyl) or an aryl group:

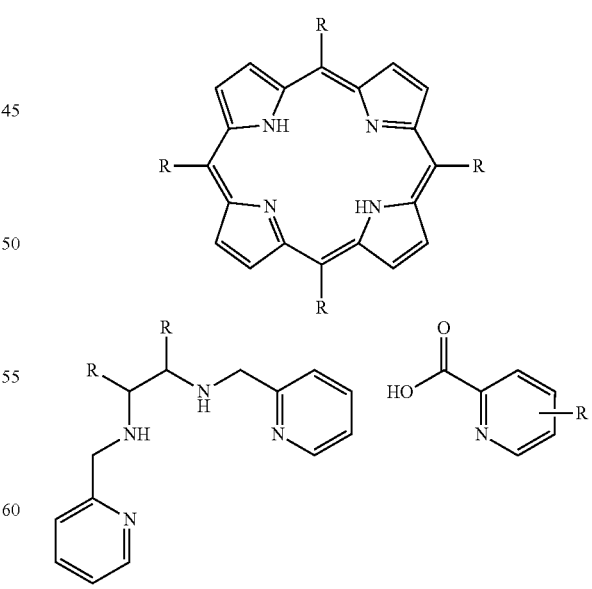

As alluded to above, compound 7, 6,7-dehydro atropine may also undergo reduction into compound 9, atropine. Preferably, one can employs a diimide reduction, where the diimide is provide from hydrazine (H2N2), in the presence of copper sulfate (CuSO₄) in ethanol (EtOH) media, which provides atropine at yields of 50%. The role of the CuSO₄ catalyst is to oxidize hydrazine to diimide in situ:

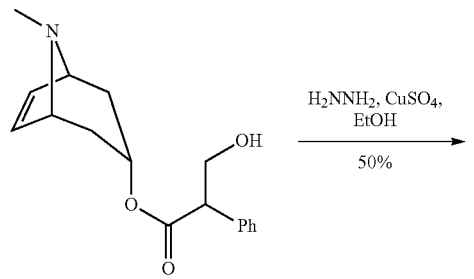

7

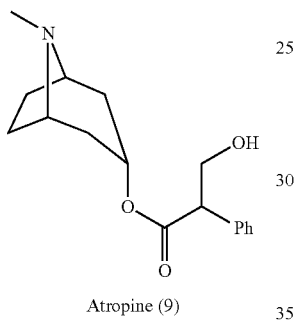

Atropine (9)

As may now be appreciated, the present invention identifies a new synthetic pathway, that allows for the ability to isolate scopolamine and/or atropine (OPNA antidotes) at the indicated yields, and in a limited number of steps, from pyrrole. Such synthetic pathway offers what is contemplated to be a significant improvement over current procedures for isolating such antidotes, an example of which is now circumventing the reliance on *Duboisia leichhardtii* as the source of scopolamine, while more efficiently meeting expanding global demands of nerve agent remedies.

What is claimed is:

1. A method for preparing 6,7-dehydro atropine comprising:

(a) providing a protected pyrrole having the following formula:

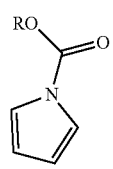

wherein R may be an alkyl group, phenyl group, or benzyl group;

(b) reacting the protected pyrrole with pentachloroacetone and forming a first tetrachloro-bicyclic compound having the following formula:

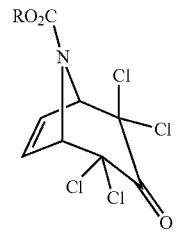

wherein R may be an alkyl group, phenyl group, or benzyl group;

(c) carrying out a reductive dechlorination of said first tetrachloro-bicyclic compound and forming a second bicyclic compound having the following formula:

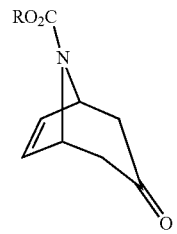

wherein R may be an alkyl group, phenyl group, or benzyl group;

(d) carrying out a reductive methylation of the second bicyclic compound formed in step (c) and forming or 8-methyl-8-azabicyclo[3.2.1]oct-6-en-3-ol having the following formula:

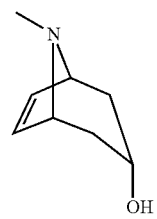

(e) converting 8-methyl-8-azabicyclo[3.2.1]oct-6-en-3-ol into 6,7-dehydro tropene tosylate having the following formula:

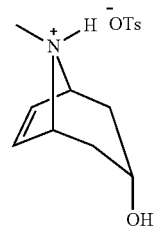

wherein ⁻OTs is reference to ⁻OSO$_2$—Ar—CH$_3$; and
(f) converting 6,7-dehydro tropene tosylate into 6,7-dehydro atropine having the following formula:

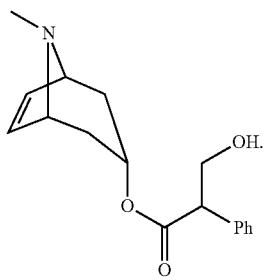 [SMILES: CN1C2C=CC1CC(OC(=O)C(CO)c1ccccc1)C2]

2. The method of claim 1 wherein 6,7-dehydro atropine is converted by oxidation into scopolamine having the following formula:

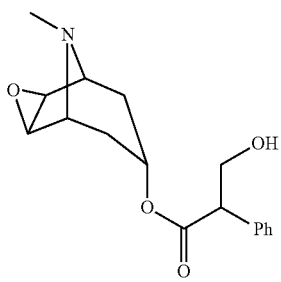 [SMILES: CN1C2CC(OC(=O)C(CO)c3ccccc3)CC1C1OC12]

3. The method of claim 2 wherein said oxidation of 6,7-dehydro atropine occurs in the presence of manganese sulfate, hydrogen peroxide and sodium bicarbonate.

4. The method of claim 1 wherein 6,7-dehydro atropine is converted by reduction into atropine having the following formula:

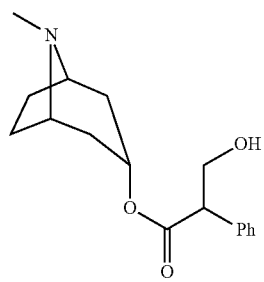 [SMILES: CN1C2CCC1CC(OC(=O)C(CO)c1ccccc1)C2]

5. The method of claim 4 wherein said reduction of 6,7-dehydro atropine occurs by diimide reduction wherein hydrazine is oxidized to a diimide in situ.

6. The method of claim 1 wherein R is a benzyl group, said first tetrachloro-bicyclic compound comprises benzyl 2,2,4,4-tetrachloro-3-oxo-8-azabicyclo[3.2.1]oct-6-ene-8-carboxylate and said second bicyclic compound comprises benzyl 3-oxo-8-azabicyclo[3.2.1]oct-6-ene-8-carboxylate.

7. The method of claim 1 wherein in step (b), said reaction of said pyrrole with pentachloroacetone takes place in the presence of N-methylmorpholine.

8. The method of claim 1 wherein in step (b), pentachloroacetone is provided in situ from hexachloroacetone.

9. A method for preparing scopolamine comprising:
(a) providing a protected pyrrole having the following formula:

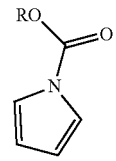

wherein R may be an alkyl group, phenyl group, or benzyl group;

(b) reacting the protected pyrrole with pentachloroacetone, wherein said pentachloroacetone is provided in situ from hexachloroacetone and forming a first tetrachloro-bicyclic compound having the following formula:

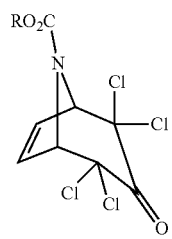

wherein R may be an alkyl group, phenyl group, or benzyl group;

(c) carrying out a reductive dechlorination of said first tetrachloro-bicyclic compound and forming a second bicyclic compound having the following formula:

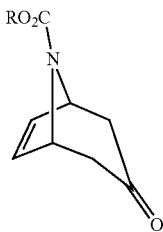

wherein R may be an alkyl group, phenyl group, or benzyl group;

(d) carrying out a reductive methylation of the second bicyclic compound formed in step (c) and forming or 8-methyl-8-azabicyclo[3.2.1]oct-6-en-3-ol having the following formula:

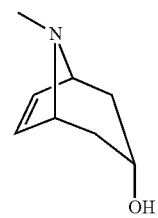

(e) converting 8-methyl-8-azabicyclo[3.2.1]oct-6-en-3-ol into 6,7-dehydro tropene tosylate having the following formula:

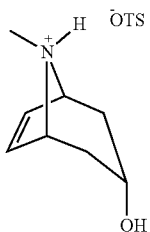

wherein ⁻OTs is reference to ⁻OSO$_2$—Ar—CH$_3$; and (f) converting 6,7-dehydro tropene tosylate into 6,7-dehydro atropine having the following formula:

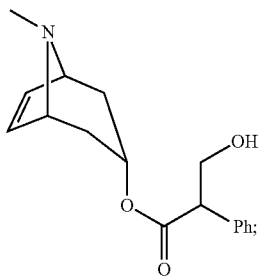 [SMILES: CN1C2C=CC1CC(OC(=O)C(CO)c1ccccc1)C2]

and (g) converting 6,7-dehydro atropine by oxidation into scopolamine having the following formula:

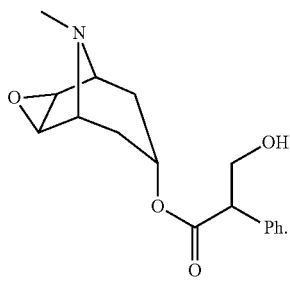 [SMILES: CN1C2CC(OC(=O)C(CO)c3ccccc3)CC1C1OC12]

10. The method of claim 9 wherein said oxidation of 6,7-dehydro atropine occurs in the presence of manganese sulfate, hydrogen peroxide and sodium bicarbonate.

11. A method for preparing atropine comprising:

(a) providing a protected pyrrole having the following formula:

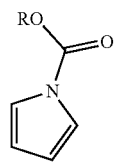

wherein R may be an alkyl group, phenyl group, or benzyl group;

(b) reacting the protected pyrrole with pentachloroacetone, wherein said pentachloroacetone is provided in situ from hexachloroacetone and forming a first tetrachloro-bicyclic compound having the following formula:

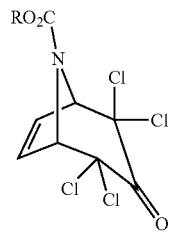

wherein R may be an alkyl group, phenyl group, or benzyl group;

(c) carrying out a reductive dechlorination of said first tetrachloro-bicyclic compound and forming a second bicyclic compound having the following formula:

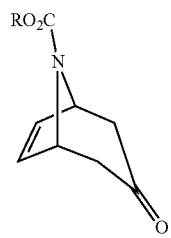

wherein R may be an alkyl group, phenyl group, or benzyl group;

(d) carrying out a reductive methylation of the second bicyclic compound formed in step (c) and forming or 8-methyl-8-azabicyclo[3.2.1]oct-6-en-3-ol having the following formula:

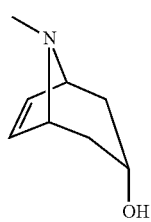

(e) converting 8-methyl-8-azabicyclo[3.2.1]oct-6-en-3-ol into 6,7-dehydro tropene tosylate having the following formula:

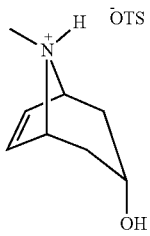

wherein $^-$OTs is reference to $^-OSO_2$—Ar—$CH_3$; and (f) converting 6,7-dehydro tropene tosylate into 6,7-dehydro atropine having the following formula:

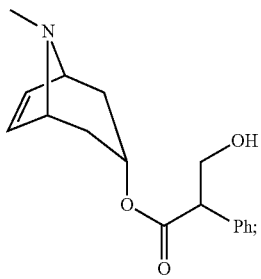 [SMILES: CN1C2C=CC1CC(OC(=O)C(CO)c1ccccc1)C2]

and converting 6,7-dehydro atropine by reduction into atropine having the following formula:

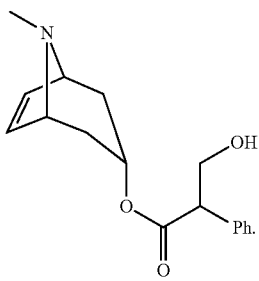 [SMILES: CN1C2C=CC1CC(OC(=O)C(CO)c1ccccc1)C2]

12. The method of claim 11 wherein said reduction of 6,7-dehydro atropine occurs by diimide reduction wherein hydrazine is oxidized to diimide in situ.

* * * * *